United States Patent
Shah

(10) Patent No.: US 8,945,662 B2
(45) Date of Patent: Feb. 3, 2015

(54) ROTARY SLIDE STAINER

(75) Inventor: Preyas Shah, Warminster, PA (US)

(73) Assignee: Rushabh Instruments, Inc., Warrington, PA (US)

(*) Notice: Subject to any disclaimer, the term of this patent is extended or adjusted under 35 U.S.C. 154(b) by 149 days.

(21) Appl. No.: 13/605,081

(22) Filed: Sep. 6, 2012

(65) Prior Publication Data

US 2014/0065291 A1 Mar. 6, 2014

(51) Int. Cl.
 *B05C 3/02* (2006.01)
 *B05D 5/00* (2006.01)
 *G01N 1/30* (2006.01)
 *B01L 9/00* (2006.01)

(52) U.S. Cl.
 CPC .... *G01N 1/30* (2013.01); *B01L 9/52* (2013.01)
 USPC ............ 427/2.11; 422/63; 422/563; 118/425; 436/46; 436/47

(58) Field of Classification Search
 CPC .................................... G01N 1/30; B01L 9/52
 See application file for complete search history.

(56) References Cited

U.S. PATENT DOCUMENTS

| | | | |
|---|---|---|---|
| 2,885,898 A * | 5/1959 | Malcom et al. | ........... 474/40 |
| 6,585,936 B1 | 7/2003 | Shah | |
| 6,883,334 B1 | 4/2005 | Shah | |
| 6,984,215 B2 | 1/2006 | Shah | |
| 7,875,242 B2 | 1/2011 | Shah | |
| 7,883,667 B2 | 2/2011 | Shah | |
| 8,158,061 B2 | 4/2012 | Shah et al. | |
| 2006/0188405 A1* | 8/2006 | Shah | ........... 422/100 |

* cited by examiner

*Primary Examiner* — Jill Warden
*Assistant Examiner* — Benjamin Whatley
(74) *Attorney, Agent, or Firm* — RatnerPrestia

(57) ABSTRACT

A slide stainer and a method for operating the slide carrier is disclosed. The slide stainer includes a slide carrier that carries one or more laboratory slides; a vessel that is capable of carrying fluid for staining the laboratory slides and that is sized to accommodate the laboratory slides; a slide transporter that moves the slide carrier into and out of the vessel; and a spring loaded pin that engages with a surface of the slide stainer to limit free-fall translation of the slide carrier in an event of a power loss. Additionally, during an agitation phase of a slide staining process, the slide transporter is configured to translate the slide carrier in an upward direction to a predetermined height that is set by a user of the slide stainer, and the slide transporter translates the slide carrier in a downward direction back into the vessel.

7 Claims, 8 Drawing Sheets

ROTARY SLIDE STAINER

FIELD OF THE INVENTION

The present invention relates to an apparatus for staining laboratory slides.

BACKGROUND OF THE INVENTION

Laboratories routinely stain biological tissue specimens deposited on laboratory slides for subsequent pathologic examination to detect and/or monitor tissue abnormalities. Automated tissue staining systems allow batch staining of large numbers of slides containing tissue specimens for subsequent examination. In the course of a staining process, the tissue specimens are exposed to a series of well-defined processing steps that ultimately produces a properly stained specimen for examination. Automation of the staining process significantly reduces the time required to stain tissue specimens, reduces the incidence of human error and allows processing parameters to be altered in an efficient manner. Improvements to slide staining systems are continually sought in the interest of reliability, performance, speed and cost.

SUMMARY OF THE INVENTION

According to one aspect of the invention, a slide stainer assembly is disclosed. The slide stainer includes a slide carrier that is configured to carry one or more laboratory slides; a vessel that is capable of carrying fluid for staining the one or more laboratory slides and sized to accommodate the one or more laboratory slides; a slide transporter that is configured to move the slide carrier into and out of the vessel; and a spring loaded pin that engages with a surface of the slide stainer to limit free-fall vertical translation of the slide carrier in an event of a power loss.

According to another aspect of the invention, a method of operating a slide stainer is disclosed. The method includes the steps of: translating a slide carrier, which is configured to carry one or more laboratory slides, in a vertical direction with respect to a vessel that is capable of carrying fluid for staining the one or more laboratory slides; and engaging a spring loaded pin with a surface of the slide stainer to limit free fall vertical translation of the slide carrier in an event of a power loss.

According to another aspect of the invention, a slide stainer includes a slide carrier that is configured to carry one or more laboratory slides; a vessel that is capable of carrying fluid for staining the one or more laboratory slides and sized to accommodate the one or more laboratory slides; a user interface for entering instructions to operate the slide stainer; and a slide transporter that is configured to move the slide carrier in and out of the vessel, and, during an agitation phase of a slide staining process, the slide transporter is configured to repeatedly (i) translate the slide carrier in an upward direction out of the vessel to a pre-determined height that is set by a user using the user interface, and (ii) translate the slide carrier in a downward direction back into the vessel.

BRIEF DESCRIPTION OF THE DRAWINGS

The invention is best understood from the following detailed description when read in connection with the accompanying drawings. It is emphasized that, according to common practice, the various features of the drawings are shown schematically and may not be to scale. Included in the drawings are the following figures.

DETAILED DESCRIPTION OF THE INVENTION

Figure 1:
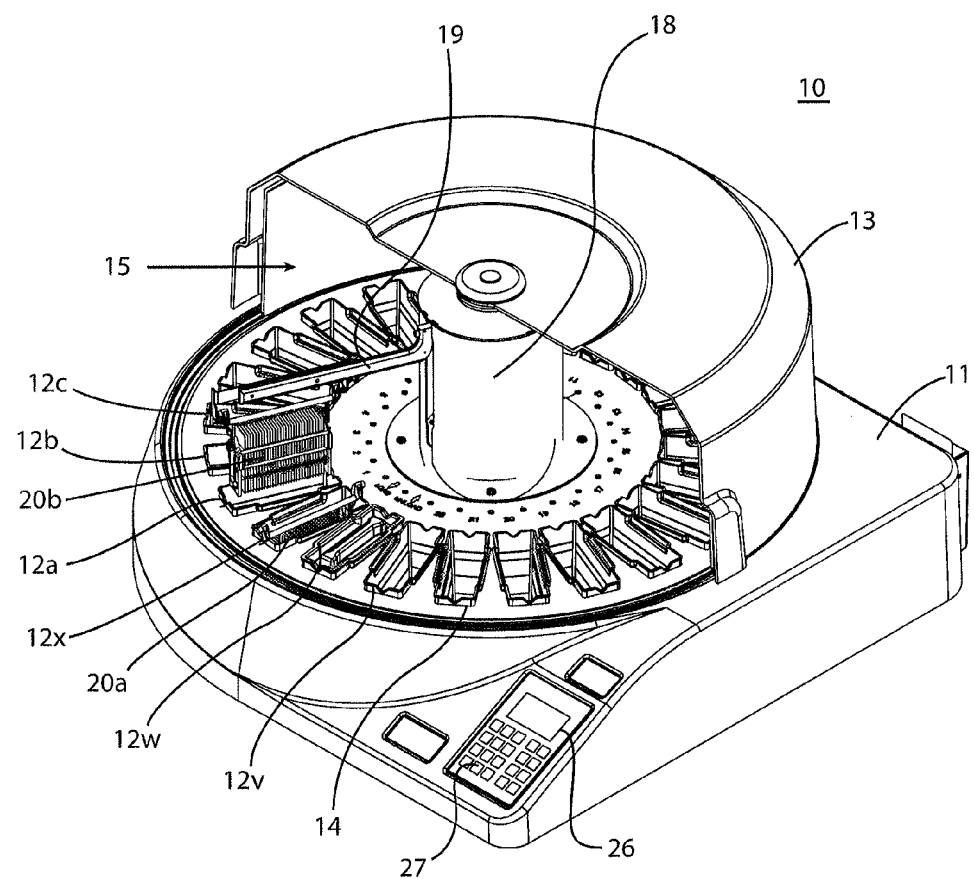
FIG. 1 depicts a perspective view of a slide stainer according to one exemplary embodiment of the invention wherein a portion of the housing cover is shown in an open configuration to reveal the interior compartment of the slide stainer.

The invention will next be illustrated with reference to the figures. Such figures are intended to be illustrative rather than limiting and are included herewith to facilitate explanation of the present invention. In the figures, like item numbers refer to like elements throughout. When a plurality of similar elements are present, a single reference numeral may be assigned to the plurality of similar elements with a small letter designation referring to specific elements. When referring to the elements collectively or to a non-specific element, the small letter designation may be omitted.

FIG. 1 depicts a perspective view of a slide stainer 10 according to one exemplary embodiment of the invention. In that figure, a portion of the two-piece top cover 13 of the housing 11 of the slide stainer 10 is shown in an open configuration (i.e., one piece of the two-piece cover 13 is rotated) to reveal the interior compartment 15 of the slide stainer 10.

The slide stainer 10 includes twenty-two (22) slide processing stations 12a through 12v, one (1) slide unloading station 12w, and one (1) slide loading station 12x. Each slide processing station 12a-12v in the illustrated embodiment includes a vessel 14 that may be filled with either a reagent for staining the slides of a single slide carrier assembly 20, or a rinsing medium, such as water, for rinsing the slides of a single slide carrier assembly 20. The slide unloading station 12w and the slide loading station 12x each includes a vessel 14 that is configured to hold a single slide carrier assembly 20.

It should be understood that any station 12 may be a staining station, a heating/drying station, a rinsing station or other type of station. Accordingly, the slide stainer 10 is not limited to the particular configuration shown. Moreover, the vessels 14 associated with stations 12a-12x may be removable from the housing 11 of the slide stainer 10, such that the stations 12 within the slide stainer 10 may be reconfigured to the operator's requirements.

Figure 2A:
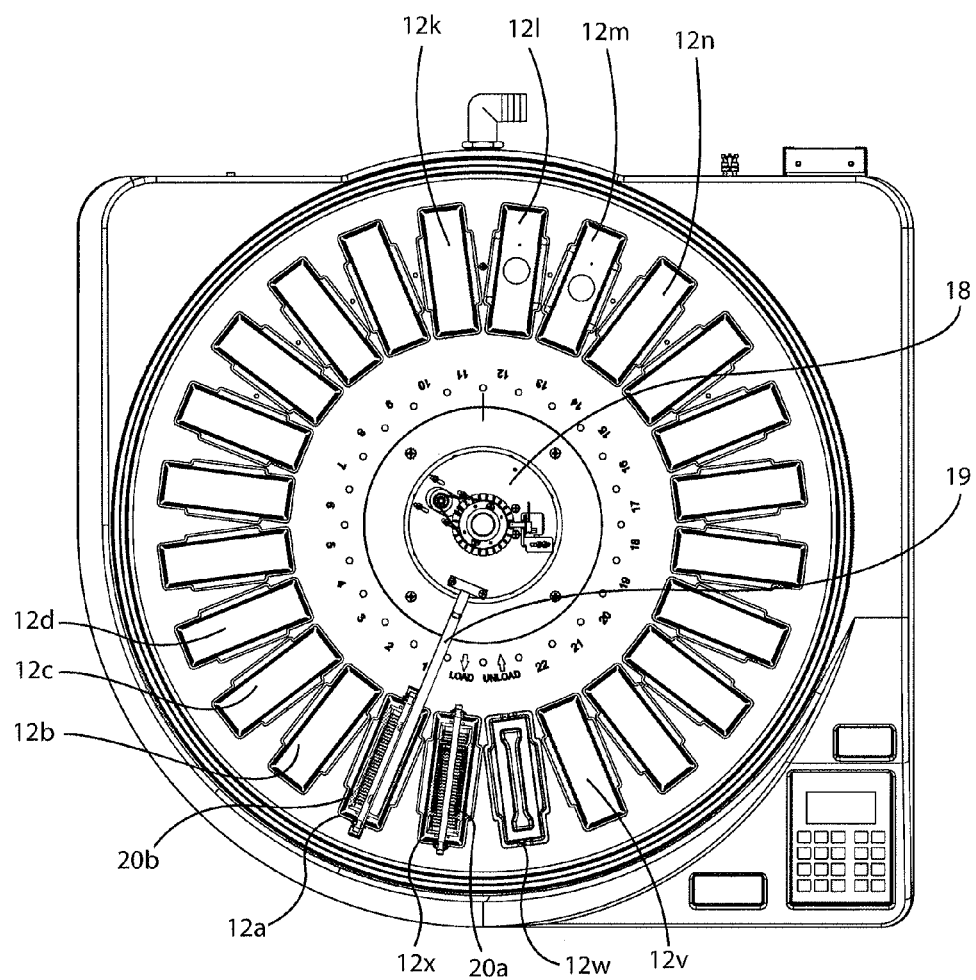
FIG. 2A depicts a top plan view of the slide stainer of FIG. 1 (housing cover omitted in its entirety), wherein the moveable arm is depicted in one radial position.
Figure 2B:
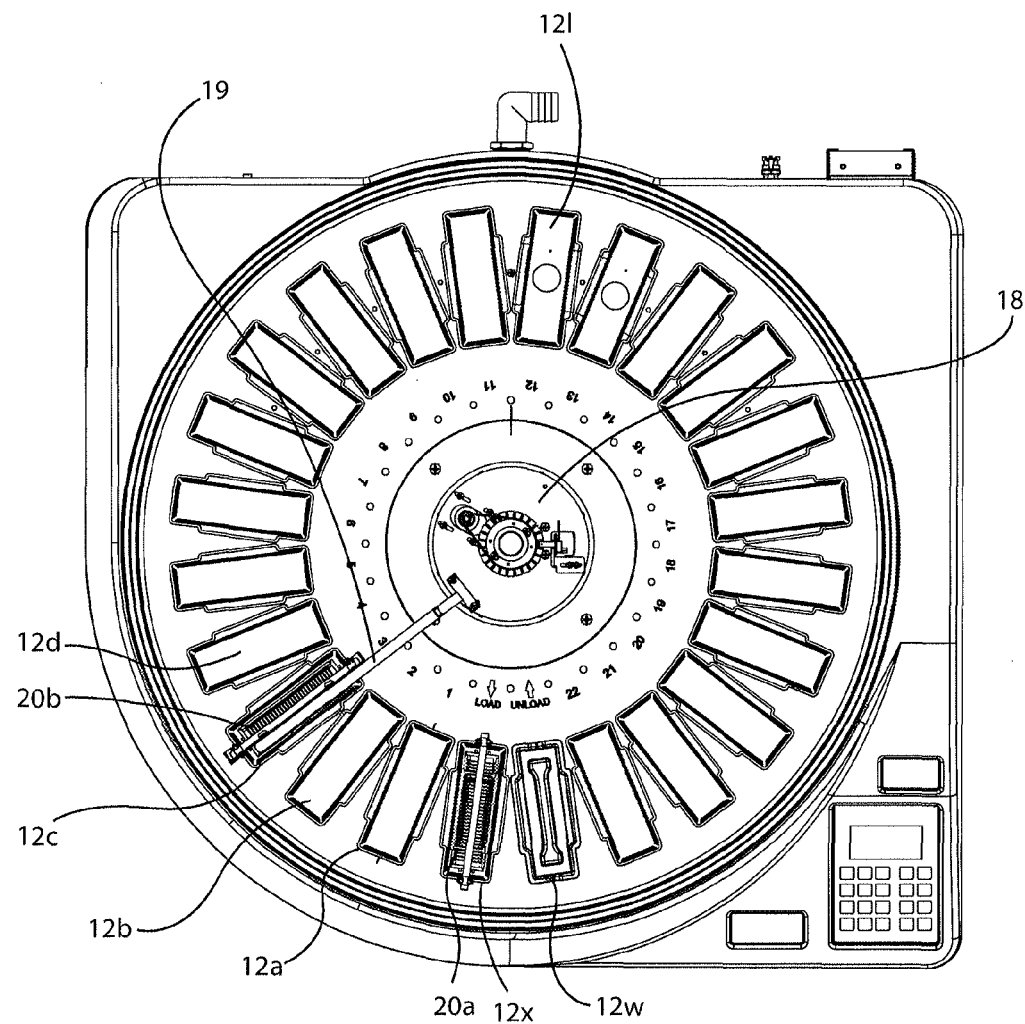
FIG. 2B depicts a top plan view of the slide stainer of FIG. 1 (housing cover omitted in its entirety), wherein the moveable arm is depicted in another radial position.
Figure 3A:
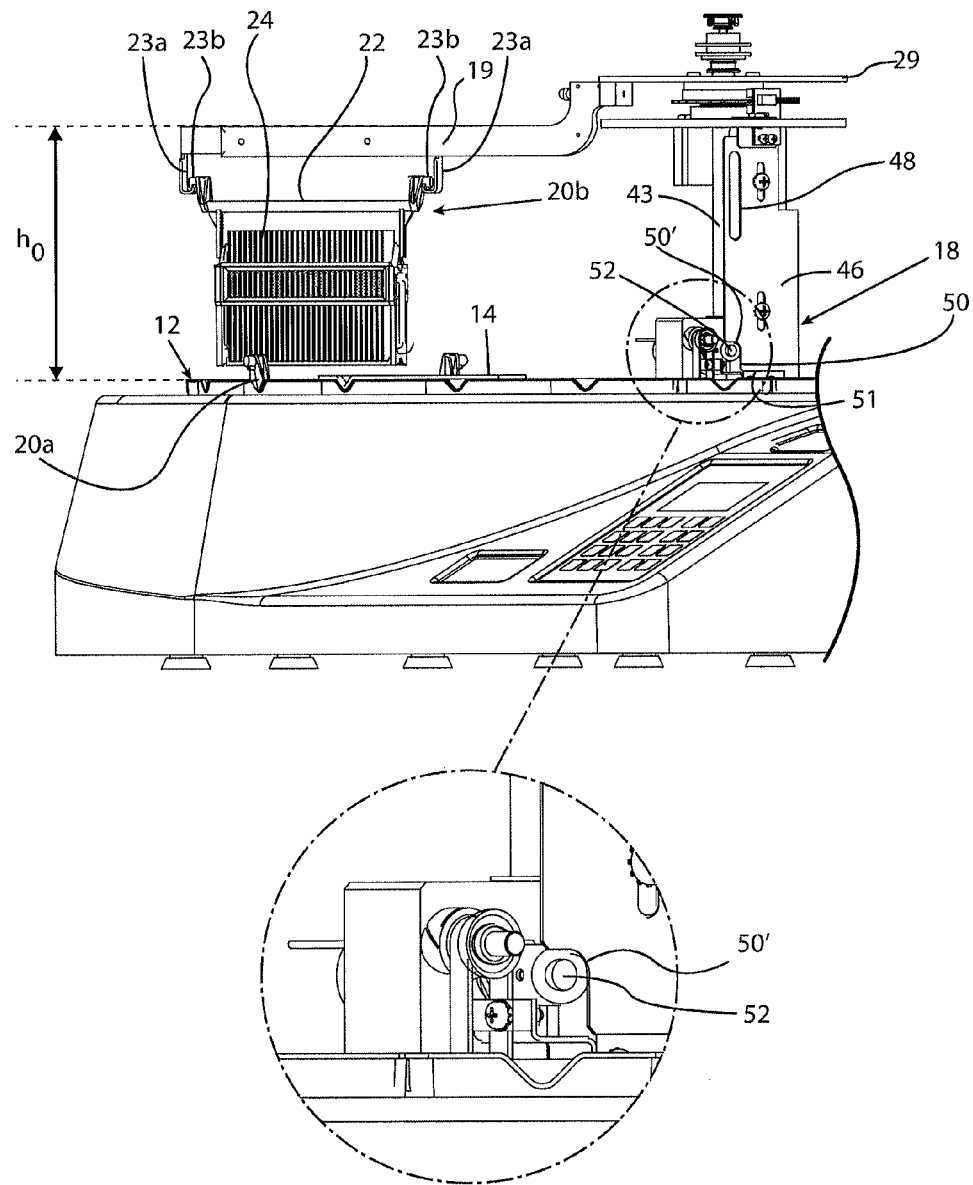
FIG. 3A depicts a side elevation view of the slide stainer of FIG. 1 (housing cover omitted in its entirety and part of the housing is cut-away), wherein the moveable arm is depicted in a raised position.

As best shown in FIG. 3A, each slide carrier assembly 20 includes a slide carrier 22 and a plurality of laboratory slides 24 releasably mounted to slide carrier 22. A laboratory specimen (not shown) is mounted to each laboratory slide 24. Two (2) slide carrier assemblies 20a and 20b are illustrated in the exemplary embodiment depicted in FIGS. 1-2B. It will be understood by those skilled in the art from the description herein that the slide stainer 10 may interface with as many as twenty-four (24) slide carrier assemblies 20.

Figure 5:
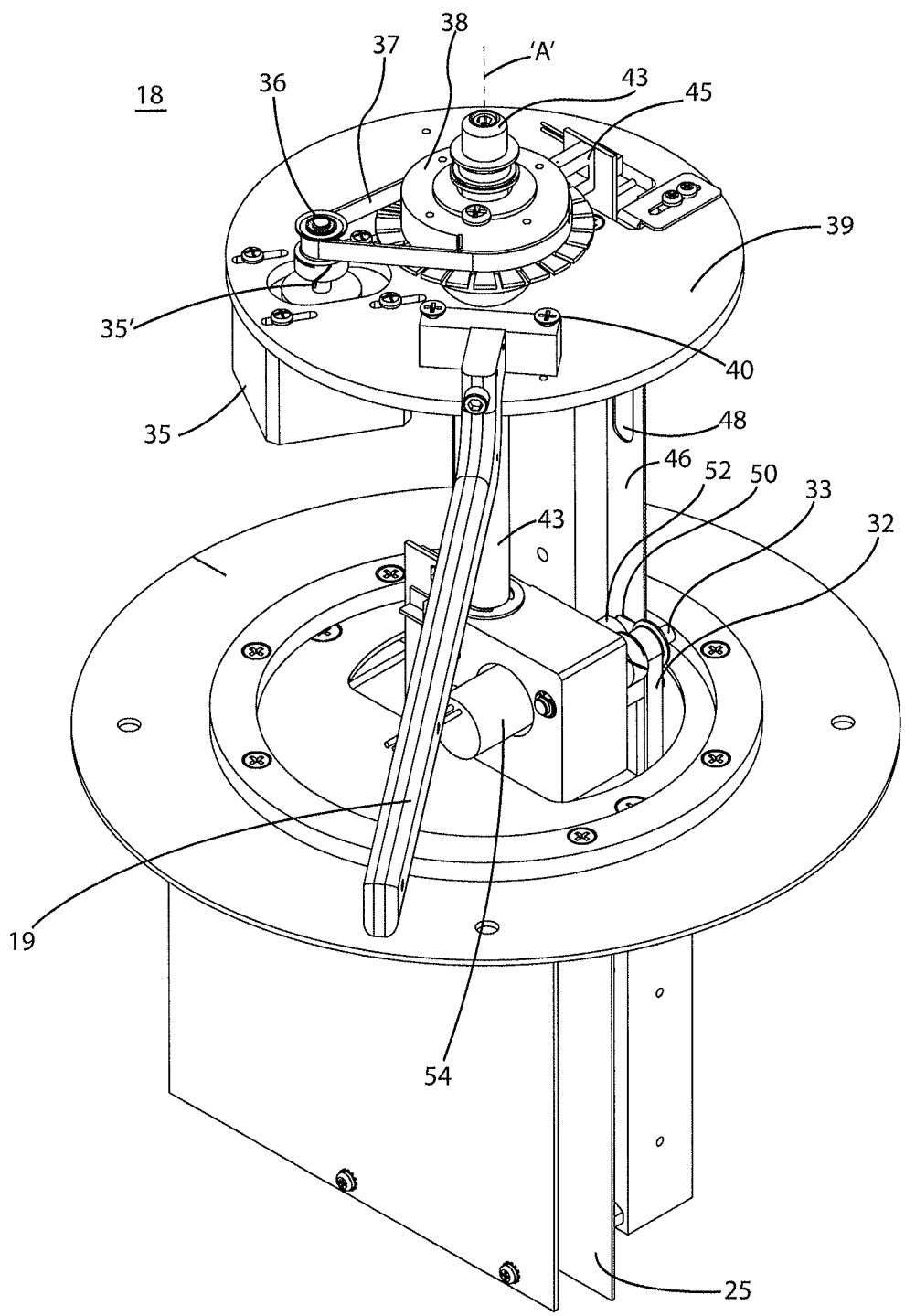
FIG. 5 depicts another perspective view of the slide transporter of FIG. 4, with the top plate of the slide transporter omitted to reveal the mechanism that accomplishes rotation of the moveable arm.

The slide stainer 10 includes an electronics control unit (ECU) 25 including a processor and controller (see FIG. 5). The ECU 25 is connected to all of the motors, solenoids and sensors that are described herein. The slide stainer 10 also includes a user interface including a user display 26 and a user keypad 27 for programming the ECU 25 of the slide stainer 10. The user interface is integrated with the housing 11 of the slide stainer 10.

The slide stainer 10 includes a slide transporter 18 that is configured to translate and rotate in order to transport a slide carrier assembly 20 from one station 12 to another station 12. The slide transporter 18 moves the slide carrier assemblies 20 in an upward direction and out of their respective vessels 14, then rotates the slide carrier assemblies 20 in either a clockwise or counterclockwise direction toward the adjacent vessels 14, and then moves the slide carrier assemblies 20 in a downward direction to position the slide carrier assemblies 20 into the adjacent vessels 14.

The slide transporter 18 includes a moveable arm 19 that is configured to rotate in both a clockwise and a counterclockwise direction (compare FIGS. 2A and 2B). FIG. 2A depicts a top plan view of the slide stainer of FIG. 1 (top cover 13 omitted in its entirety), wherein the moveable arm 19 is positioned above station 12a. FIG. 2B depicts the moveable arm 19 of the slide transporter 18 rotated in a clockwise direction with respect to its position in FIG. 2A such that the moveable arm 19 is positioned above station 12c.

Figure 3B:
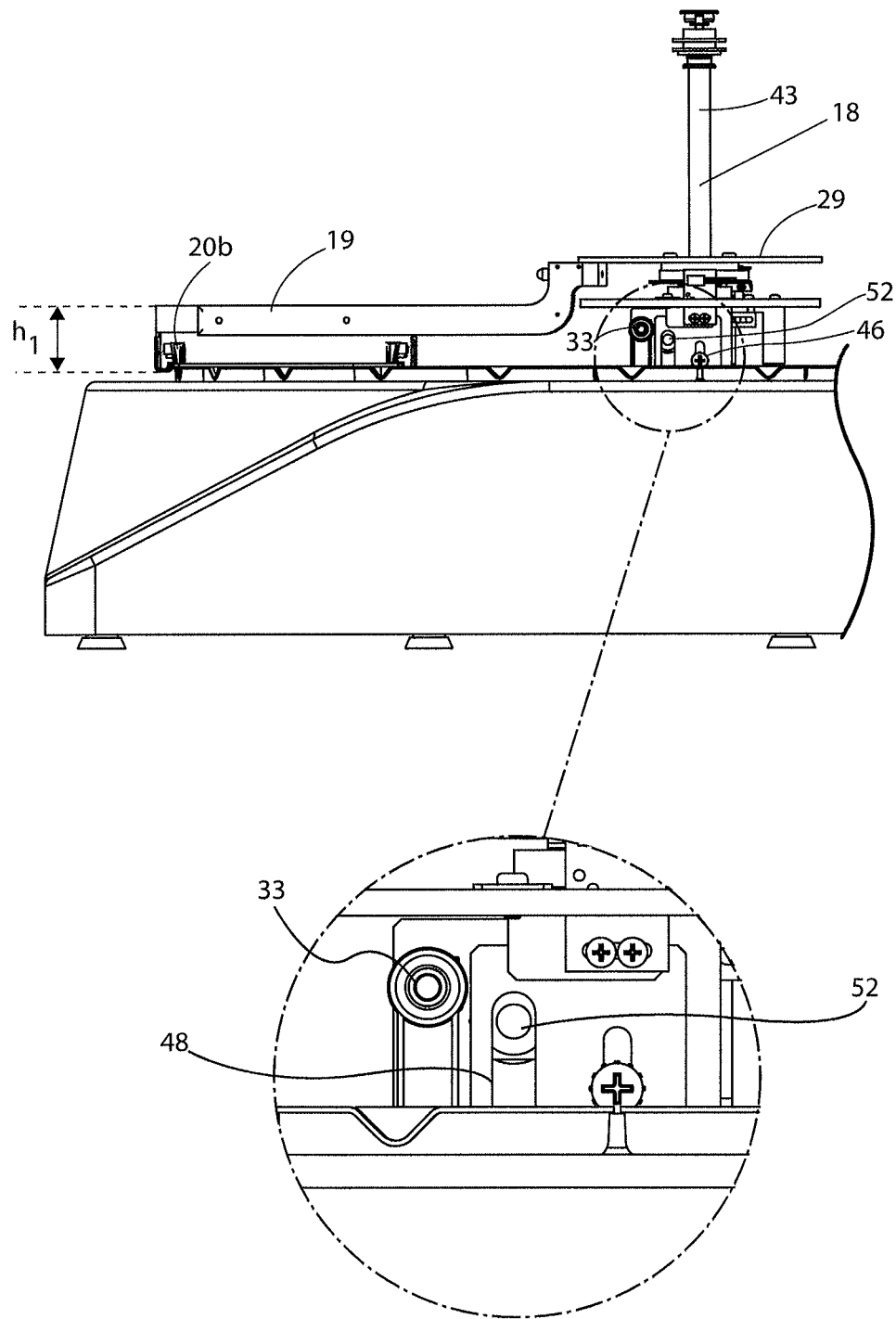
FIG. 3B depicts a side elevation view of the slide stainer of FIG. 1 (housing cover omitted in its entirety and part of the housing is cut-away), wherein the moveable arm is depicted in a lowered position.

The slide transporter 18 is also configured to translate the moveable arm 19 in a vertical direction (compare FIGS. 3A and 3B). FIG. 3A depicts the moveable arm 19 in a raised position, where the distance between the arm 19 and the top surface of the stations 20 is designated by height $h_0$. At height $h_0$, the slide carrier assembly 20b that is coupled to the moveable arm 19 is positioned above the stations 12 such that the carrier assembly 20b is not positioned in a vessel 14 of a station 12. FIG. 3B depicts the moveable arm 19 in a lowered position, where the distance between the arm 19 and the top surface of the stations 20 is designated by height $h_1$. At height $h_1$, the slide carrier assembly 20b that is coupled to the moveable arm 19 is positioned in a vessel 14 of a station 12.

The slide transporter 18 can be programmed to maintain the moveable arm 19 at any desired height between height $h_1$ and height $h_0$. An operator of the slide stainer 10 can select from multiple heights for the moveable arm 19 during an agitation phase of the slide staining process. More particularly, during the agitation phase of the slide staining process, the slide stainer 10 moves the arm 19 up and down to repeatedly dunk the slides 24 in their respective vessels 14, thereby agitating the reagent in the respective vessels 14. The operator may change the vertical height 'h' at which the arm 19 travels to tailor the intensity of the agitation phase.

The moveable arm 19 includes means for releasably carrying a single slide carrier assembly 20. The releasable slide carrying means of the moveable arm 19 may be brackets 23a (see FIG. 3A) having recesses that are configured to releasably engage posts 23b that extend from the sides of the slide carrier assembly 20. The releasably carrying means may also be in the form of a slot, fastener, surface, recess, protrusion, magnet, or pin, for example.

Referring now to the basic operation of the slide stainer 10, an operator of the slide stainer 10 manually loads a slide carrier assembly 20 into the load station 12x. The slide transporter 18 sequentially transports the slide carrier assembly 20 from the load station 12x to one or more stations 12a-12w under the control of the ECU 25. The operator then manually removes a processed slide carrier assembly 20 from the unload station 12w.

Figure 4:
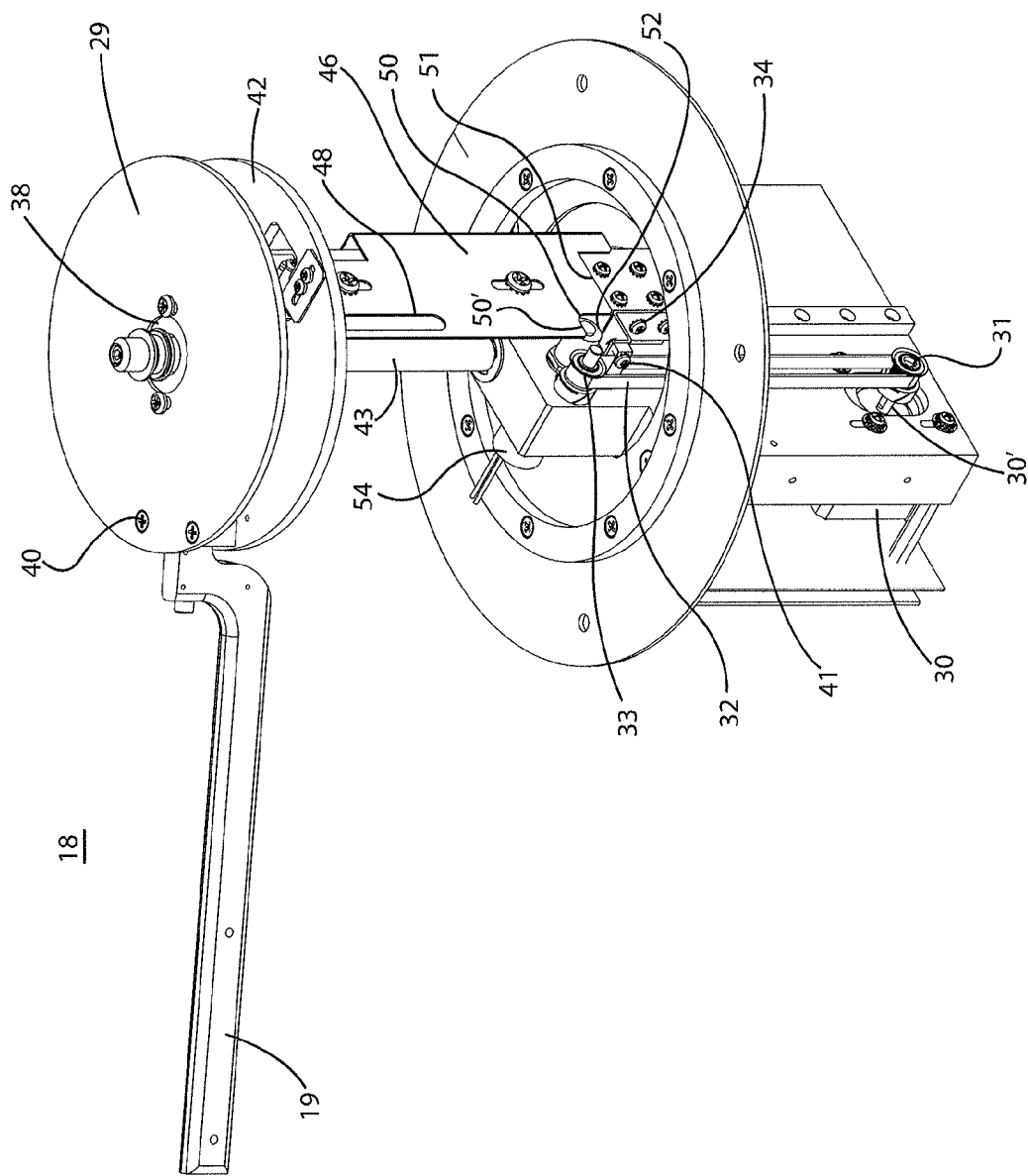
FIG. 4 depicts a perspective view of the slide transporter of the slide stainer of FIG. 1.

The operation of the slide transporter 18 will now be described in greater detail. FIG. 4 depicts a perspective view of the slide transporter 18 of the slide stainer 10 of FIG. 1. FIG. 5 depicts another perspective view of the slide transporter 18 of FIG. 4, with the top plate 29 omitted. As will be described in greater detail hereinafter, an arrangement of motors, gears, belts and sensors are configured for rotating and translating the moveable arm 19 to any desired position.

As best shown in FIG. 4, to accomplish vertical translation of the moveable arm 19 along vertical axis 'A,' the slide transporter 18 includes a motor 30 having a rotatable output shaft 30'. A belt pulley 31 is connected to the rotatable output shaft 30' of the motor 30. A belt 32 is attached to the belt pulley 31 and another belt pulley 33. A bracket 34 is attached to the belt 32 by a fastener 41 such that the bracket 34 moves along with the belt 32. The bracket 34 is indirectly fixed to the moveable arm 19 such that the moveable arm 19 translates along with the bracket 34.

More particularly, the bracket 34 is fixedly attached to another bracket 46, and the bracket 46 is fixedly attached to a lower plate 42. The lower plate 42 is fixedly attached to the top plate 29. The arm 19 is fixedly attached to the bottom side of the top plate 29 by fasteners 40. Thus, the brackets 34 and 46, the plates 42 and 29 and the arm 19 all simultaneously translate together in a vertical direction (i.e., along axis A). The plates 29 and 42 translate along the length of a fixed post 43 (compare FIGS. 3A and 3B).

In operation, rotation of the output shaft 30' of the motor 30 causes rotation of the belt pulley 31, which causes rotation of the belt 32. The bracket 34 translates in a vertical direction as the belt 32 rotates. The moveable arm 19 translates in a vertical direction along with the bracket 34. Thus, rotation of the output shaft 30' of the motor 30 causes translation of the moveable arm 19 in a vertical direction. The output shaft 30' can rotate in a counterclockwise direction (taken from the perspective of FIG. 4) to raise the arm 19, or the output shaft 30' can rotate in a counterclockwise direction to lower the arm 19.

Although not shown, a sensor monitors the movement of the output shaft 30', the belt 32, the arm 19, the bracket 34 and/or the bracket 46 and transmits a corresponding signal to the ECU 25. The sensor may be a hall sensor or a rotary encoder. The ECU 25 monitors that signal to determine when the moveable arm 19 has reached its intended vertical position. Once the arm 19 has reached its intended vertical position, the ECU 25 deactivates the motor 30. Those skilled in the art will recognize that numerous ways exist to monitor the vertical position of the arm 19.

As best shown in FIGS. 4 and 5, to accomplish rotation of the moveable arm 19 about the axis of rotation 'A,' the slide transporter 18 includes a motor 35 having a rotatable output shaft 35'. A belt pulley 36 is connected to the rotatable output shaft 35' of the motor 35. A belt 37 is attached to the belt pulley 36 and another belt pulley 38. The belt pulley 38 is fixedly attached to the top plate 29 (see FIG. 4). The top plate 29 is fixedly attached to the arm 19 by fasteners 40 (see FIG. 4).

In operation, rotation of the output shaft 35' of the motor 35 causes rotation of the belt pulley 36, which causes rotation of the belt 37, which causes rotation of the belt pulley 38, which causes rotation of the top plate 29, which causes rotation of the moveable arm 19. Thus, rotation of the output shaft 35' of the motor 35 ultimately causes rotation of the moveable arm 19. The output shaft 35' can rotate in either a counterclockwise direction to rotate the arm 19 in a counterclockwise direction, or rotate in a clockwise direction to rotate the arm 19 in a clockwise direction.

A sensor 45, such as a hall sensor, an optical sensor, or a rotary encoder, for example, monitors the movement of the belt pulley 38 and transmits a corresponding signal to the ECU 25. The ECU 25 monitors that signal to determine when the moveable arm 19 has reached its intended rotational position. Once the arm 19 has reached its intended rotational position, the ECU 25 deactivates the motor 35. Those skilled in the art will recognize that numerous ways exist to monitor the rotational position of the arm 19.

Referring now to FIGS. 3A, 3B and 4, an elongated slot 48 is formed at the top end of the bracket 46, and a recess 50 is formed at the bottom end of the bracket 46. The recess 50 extends between a top edge 50' and a bottom edge 51 of the bracket 46. As will be described later, the recess 50 interacts with a pin 52.

The pin 52 includes an internal compression spring that biases the pin 52 in an outward direction toward the bracket 46. The pin 52 is also actuated by a solenoid 54 that cooperates with the pin 52. The solenoid 54 is, however, an optional component of the slide stainer 10. Upon activating the solenoid 54, the magnetic field produced by the solenoid 54 draws the spring-loaded pin 52 inward (i.e., toward the solenoid 54 and away from the bracket 46) to a retracted position against the bias of its internal compression spring. Once deactivated or in the event of a power loss, the magnetic field is severed and the compression spring of the spring-loaded pin 52 biases the pin 52 outward (i.e., away from the solenoid 54 and toward the bracket 46) to an extended position.

In operation, when the moveable arm 19 is translated in a downward vertical direction and approaches height $h_1$, the solenoid 54 may be deactivated to conserve power, which causes the pin 52 to spring forward toward the bracket 46 and through the elongated slot 48 under the force of the compression spring to the extended position.

When the moveable arm 19 is translated in an upward vertical direction and approaches height $h_0$ (see FIG. 3A), the solenoid 54 is deactivated thereby releasing the pin 52 to both conserve power and prepare for a potential power loss. Consequently, the pin 52 springs forward under the force of the compression spring (not shown) toward the bracket 46 to the extended position. The extended pin 52 either approaches or bears upon the top edge 50' of the recess 50. Thus, in the event of a power loss, the engagement between the extended pin 52 and the top edge 50' of the recess 50 prevents the arm 19 and all of the components that are either directly or indirectly connected to the arm 19 from free-falling in a downward vertical direction under gravity.

While some conventional slide stainers employ a leadscrew to accomplish safe vertical translation of the slide carriers, such leadscrews can be expensive and may require significant torque from a motor. This invention offers a cost-effective way to accomplish safe vertical translation of the slide carriers while preventing damage to the slide stainer in the event of a power outage.

Figure 6:
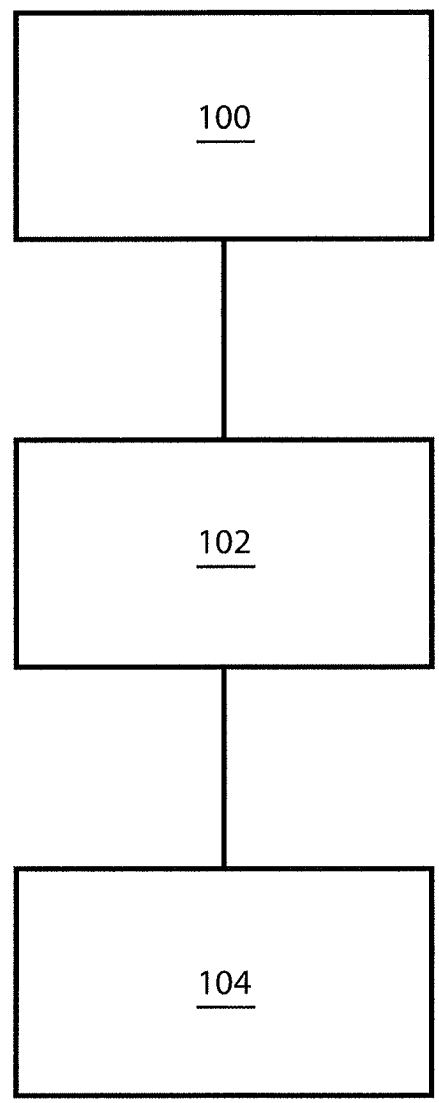
FIG. 6 is a flow chart depicting an exemplary method for operating the slide stainer.

FIG. 6 is a flow chart depicting an exemplary method of operating the slide stainer 10. At step 100, the solenoid 54 is activated to retract the spring-loaded pin 52 thereby disengaging the pin 52. At step 102, the slide carrier 20 is translated in a vertical direction with respect to the vessel 14. In the course of step 102, the belt 32 that is indirectly attached to the slide carrier 20 translates the slide carrier 20 in a vertical direction, as described previously.

At step 104, the solenoid 54 that cooperates with the spring-loaded pin 52 is deactivated causing the spring-loaded pin 52 to extend under its own spring force into the recess 50 of the bracket 46. In an event of a power loss, the spring loaded pin 52 would ultimately engage with a surface (e.g., edge 50') of the slide stainer 10 to limit free fall vertical translation of the slide carrier 20.

While exemplary embodiments of the invention have been shown and described herein, it will be understood that such embodiments are provided by way of example only. Numerous variations, changes and substitutions will occur to those skilled in the art without departing from the spirit of the invention. For example, the spring-loaded pin 52 may be positioned on the bracket 46 (or other translating component of the slide stainer 10) and the slot 46 and/or the recess 50 may be defined on a fixed component of the slide stainer 10 to achieve the same result. Accordingly, it is intended that the appended claims cover all such variations as fall within the spirit and scope of the invention.

What is claimed:

1. A slide stainer comprising:
   a slide carrier that is configured to carry one or more laboratory slides;
   a vessel that is capable of carrying fluid for staining the one or more laboratory slides and sized to accommodate the one or more laboratory slides;
   a slide transporter that is configured to move the slide carrier in a vertical direction into and out of the vessel, the slide transporter comprising a bracket, the bracket being either directly or indirectly attached to the slide carrier; and
   a spring loaded pin that is moveable in a horizontal direction with respect to the slide carrier between an extended position and a retracted position, wherein, in the extended position, the spring loaded pin engages with a surface of the bracket of the slide stainer to limit free-fall vertical translation of the slide carrier in an event of a power loss.

2. The slide stainer of claim 1, wherein the slide transporter is configured to rotate the slide carrier about an axis of rotation of the slide transporter.

3. The slide stainer of claim 2, further comprising a plurality of vessels that are radially positioned about the axis of rotation, the slide transporter being configured to move the slide carrier to each of the plurality of vessels.

4. The slide stainer of claim 1, further comprising a solenoid that cooperates with the spring loaded pin to retract the spring loaded pin thereby separating the pin from said surface of the slide stainer.

5. The slide stainer of claim 1, wherein, to accomplish the vertical translation of the slide carrier, the slide transporter further comprises a motor, a belt attached to an output shaft of the motor, the bracket being attached to the belt, wherein rotation of the output shaft induces the vertical translation of the slide carrier.

6. The slide stainer of claim 1, wherein the slide transporter is not driven in a vertical direction by a leadscrew.

7. The slide stainer of claim 1, wherein said surface of the slide stainer is an edge of a hole, slot or recess that is formed in the bracket that translates along with the slide carrier.

* * * * *